(12) United States Patent
Khokhlova et al.

US008668658B2

(10) Patent No.: US 8,668,658 B2
(45) Date of Patent: Mar. 11, 2014

(54) DERATING METHOD FOR THERAPEUTIC APPLICATIONS OF HIGH INTENSITY FOCUSED ULTRASOUND

(75) Inventors: Vera A. Khokhlova, Seattle, WA (US); Olga V. Bessonova, Moscow (RU); Michael S. Canney, Menomonee Falls, WI (US); Michael R. Bailey, Seattle, WA (US); Oleg A. Sapozhnikov, Seattle, WA (US); Lawrence A. Crum, Bellevue, WA (US)

(73) Assignee: University of Washington, Seattle, WA (US)

( * ) Notice: Subject to any disclaimer, the term of this patent is extended or adjusted under 35 U.S.C. 154(b) by 77 days.

(21) Appl. No.: 13/236,531

(22) Filed: Sep. 19, 2011

(65) Prior Publication Data

US 2012/0071795 A1 Mar. 22, 2012

Related U.S. Application Data

(60) Provisional application No. 61/384,108, filed on Sep. 17, 2010.

(51) Int. Cl.
*A61H 1/00* (2006.01)
(52) U.S. Cl.
USPC .......................................................... 601/2
(58) Field of Classification Search
USPC .......................................................... 601/2
See application file for complete search history.

(56) References Cited

U.S. PATENT DOCUMENTS 7,600,410 B2 10/2009 Sliwa, Jr. et al.

OTHER PUBLICATIONS

Averkiou, M. et al., "Modeling of an Electrohydraulic Lithotripter with the KZK Equation," Journal of Acoustical Society of America, Jul. 1999, pp. 102-112.
Bessonova, O. et al., "A Derating Method for Therapeutic Applications of High Intensity Focused Ultrasound," Acoustical Physics, 2010, vol. 56, No. 3, pp. 380-390.
Bessonova, O. et al., "Nonlinear Derating Method for High Intensity Focused Ultrasound (HIFU) Fields," 2009 IEEE International Ultrasound Symposium Proceedings, pp. 216-219.
Canney, M. et al., "Acoustic Characterization of High Intensity Focused Ultrasound Fields: A Combined Measurement and Modeling Approach," Journal of Acoustical Society of America, vol. 124, No. 4, Oct. 2008, pp. 2406-2420.
Cheung, T.Y., "Thesis: Application of the Khokhlov-Zabolotskaya-Kuznetsov Equation to Modeling High-Intensity Focused Ultrasound Beams," Boston University, College of Engineering, Submitted in partial fulfillment of the requirements for the degree of Master of Science, 2010, 57 pages.
Khokhlova, T. et al., "Magnetic Resonance Imaging of Boiling Induced by High Intensity Focused Ultrasound," Journal of Acoustical Society of America, vol. 125, No. 4, Apr. 2009, pp. 2420-2431.
Khokhlova, T. et al., "Millisecond Bursts of Focused Ultrasound Shock Waves to Produce Boiling and Tissue Emulsification," Submitted as a regular research paper for the Special Issue on the Acoustics of Bubbles and Cavitation (ABC), 2011, 41 pages.

*Primary Examiner* — Tse Chen
*Assistant Examiner* — Hien Nguyen
(74) *Attorney, Agent, or Firm* — Perkins Coie LLP

(57) ABSTRACT

Methods of derating a nonlinear ultrasound field and associated systems are disclosed herein. A method of derating a nonlinear ultrasound field in accordance with an embodiment of the present technology can include, for example, calibrating an ultrasound source to a first source voltage ($V_w$) and generating a nonlinear acoustic wave from the ultrasound source into water. The method can further include measuring a focal waveform of the nonlinear acoustic wave and determining a second source voltage ($V_t$) of the ultrasound source that generates the same focal waveform in tissue.

20 Claims, 12 Drawing Sheets

| HIFU TRANSDUCER FOCUSING IN WATER | | HIFU TRANSDUCER FOCUSING IN TISSUE | | PRESSURES AT THE FOCUS | | |
|---|---|---|---|---|---|---|
| Voltage $V_W$, mV | Pressure Amplitude $p_0$, MPa | Voltage $V_t$, mV | Pressure Amplitude $p_0$, MPa | Peak Negative Pressure $p_{-F}$, MPa | Peak Positive Pressure $p_{+F}$, MPa | Shock Amplitude $A_s$, MPa |
| 50 | 0.048 | 82.3 | 0.079 | 2.12 | 2.52 | |
| *100* | *0.096* | *164* | *0.159* | *3.95* | *5.61* | |
| 150 | 0.147 | 247 | 0.242 | 5.62 | 9.77 | |
| 200 | 0.197 | 329 | 0.324 | 7.07 | 15.2 | |
| 250 | 0.244 | 411 | 0.403 | 8.31 | 22.7 | |
| *300* | *0.294* | *494* | *0.485* | *9.48* | *35.3* | *25.6* |
| 350 | 0.343 | 576 | 0.566 | 10.5 | 53.0 | 39.8 |
| *400* | *0.389* | *659* | *0.642* | *11.4* | *63.6* | *49.1* |
| 450 | 0.437 | 741 | 0.721 | 12.3 | 69.9 | 55.4 |
| 500 | 0.485 | 823 | 0.799 | 13.2 | 74.6 | 61.4 |
| 550 | 0.530 | 906 | 0.874 | 13.9 | 77.7 | 67.2 |
| *600* | *0.567* | *988* | *0.934* | *14.5* | *80.3* | *71.3* |
| 650 | 0.590 | 1070 | 0.972 | 14.8 | 80.9 | 75.9 |
| 700 | 0.612 | 1153 | 1.008 | 15.1 | 82.5 | 78.6 |
| 750 | 0.640 | 1235 | 1.055 | 15.5 | 83.9 | 82.0 |

DERATING METHOD FOR THERAPEUTIC APPLICATIONS OF HIGH INTENSITY FOCUSED ULTRASOUND

CROSS-REFERENCE TO RELATED APPLICATION(S)

This application claims the benefit of U.S. Provisional Patent Application No. 61/384,108, filed Sep. 17, 2010, entitled "A DERATING METHOD FOR THERAPEUTIC APPLICATIONS OF HIGH INTENSITY FOCUSED ULTRASOUND," which is incorporated herein by reference in its entirety.

STATEMENT REGARDING FEDERALLY SPONSORED RESEARCH OR DEVELOPMENT

This invention was made with government support under R01EB007643 awarded by National Institutes of Health (NIH)—Federal Reporting, SMST0601 awarded by National Space Biomedical Research Institute (NSBRI). The government has certain right in the invention.

TECHNICAL FIELD

The present technology relates generally to derating methods. In particular, several embodiments are directed toward nonlinear derating methods for high intensity focused ultrasound systems.

BACKGROUND

High intensity focused ultrasound systems are used in various medical ultrasound applications. During diagnostic ultrasound procedures, for example, high intensity ultrasound energy can be pulsed in a Doppler or harmonic imaging mode to propagate nonlinear waves. The harmonic frequencies of the nonlinear waves have a higher contrast to noise ratio than that of the fundamental frequency, and therefore enhance the resolution of ultrasound imaging. In therapeutic ultrasound applications, high intensity focused ultrasound energy can be radiated toward a focal region in tissue (e.g., tumors, cancerous tissue regions, bleeding spots). The accumulation of the harmonic frequencies causes rapid heating at the focal region that ablates, necrotizes, and/or otherwise damages the tissue. Rapid heating can cause boiling in tissue in the focal region. Predicting the parameters of such high intensity focused acoustic fields in situ can be important for planning treatment protocols, anticipating ultrasound-induced bioeffects in tissue, and developing safety and efficacy standards for high intensity ultrasound.

A process known as "derating" can be used to estimate the parameters of an acoustic field in situ. During a typical derating process, acoustic field measurements are taken in water at low level ultrasound source outputs. The measured values are then linearly extrapolated to account (1) for higher source outputs used in medical procedures and (2) for tissue attenuation. For example, a measured source pressure can be scaled linearly to obtain the focal pressure amplitude in water, and the linearly scaled focal pressure can then be derated by a compensation factor that depends on the propagation path (i.e., the focal distance) and the linear attenuation coefficient of tissue to determine the focal pressure in tissue.

When working with high intensity diagnostic and therapeutic ultrasound applications that produce nonlinear acoustic fields, the assumption of linear acoustic propagation introduces errors into the derating process. For example, the wave intensity at the focus is not a quadratic function of the pressure amplitude at the fundamental frequency, but instead consists of contributions from all of the harmonics. Similarly, the heating rate at the focus is not proportional to the intensity at the focus due to the contribution of more readily absorbed higher frequency components. Accordingly, linear derating is generally unsuitable for the estimation of nonlinear acoustic field parameters in tissue.

DETAILED DESCRIPTION

The present technology is directed toward nonlinear derating methods for high intensity focused ultrasound systems. In several embodiments, a nonlinear derating method measures and/or models focal waveforms in water, and scales source outputs to generate the same focal waveform with the same focal pressure and focal shape in tissue. The pressure amplitude at the focus of HIFU sources having high focusing gains (e.g., between 20 and 50) is significantly higher than on the way to the focus and the length of the focal region is much shorter than the focal length. Without being bound by theory, it is thought that this causes the nonlinear effects in the high amplitude focus to dominate prefocal nonlinear propagation. Additionally, it is thought that the degree of nonlinear waveform distortion at the focus can be determined using the pressure levels in the focal region, and that the attenuation in tissue on the way to the focus can be determined using the operational frequency of the source. Therefore, the nonlinear derating method can use focal waveforms measured or modeled in water to determine parameters of nonlinear ultrasound fields in tissue for planning treatment protocols and for the development of safety and efficacy standards for high intensity ultrasound systems.

Certain specific details are set forth in the following description and in FIGS. 1-11B to provide a thorough understanding of various embodiments of the technology. For example, embodiments of nonlinear derating methods are discussed in relation to high intensity focused ultrasound ("HIFU") systems that form shock waves in tissue in the focus. The present technology, however, may be used to predict acoustic field parameters of other therapeutic and diagnostic ultrasound systems that propagate focused nonlinear acoustic waves. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-11B.

Figure 1:
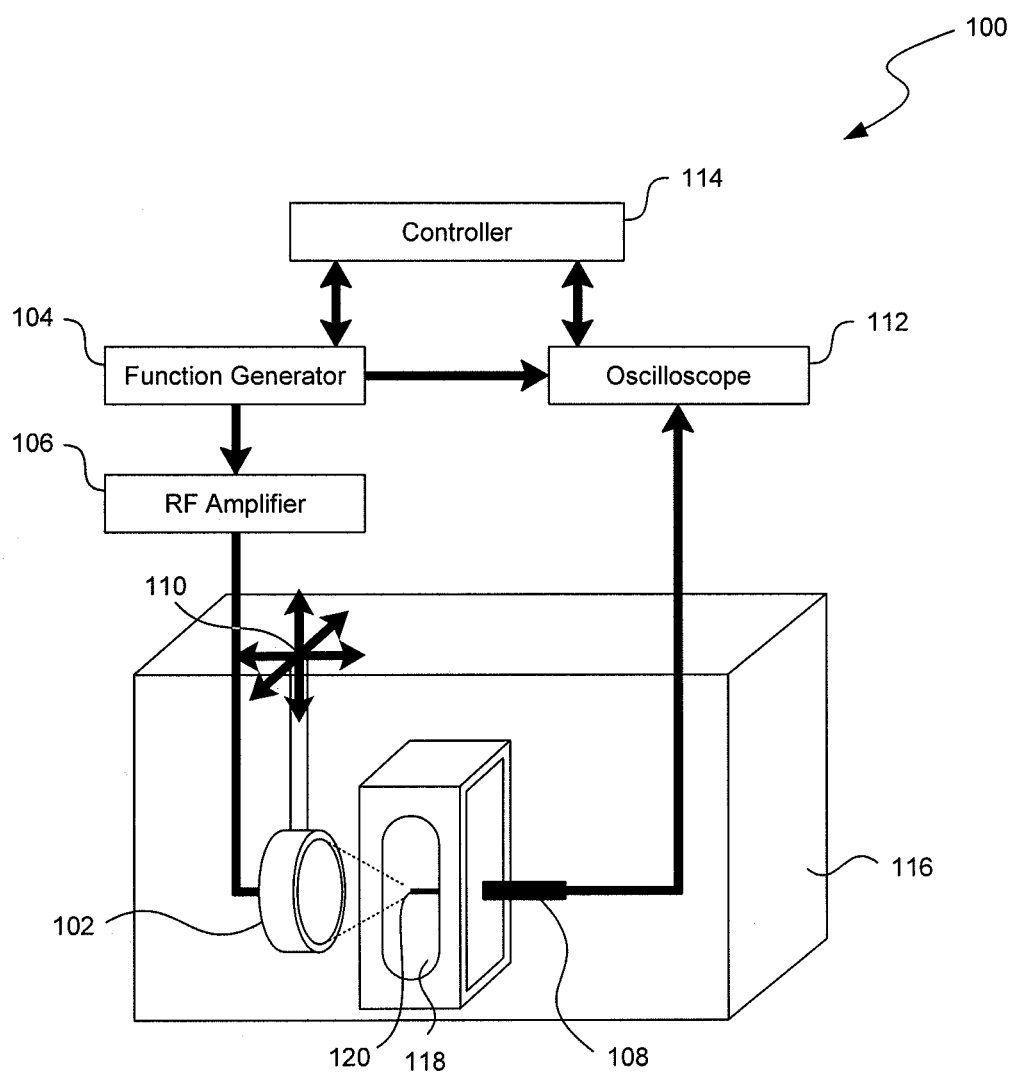
FIG. 1 is a schematic view of an ultrasound system configured in accordance with an embodiment of the present technology.

FIG. 1 is a schematic view of an ultrasound system 100 ("system 100") configured in accordance with an embodiment of the present technology. The system 100 can include a function generator 104 and an amplifier 106 operably coupled to an ultrasound source 102 ("source 102"). The function generator 104 can be an Agilent 33250A function generator made by Agilent Technologies of Palo Alto, Calif., and the amplifier 106 can be an ENI A-300 RF amplifier made by Electronic Navigation Industries of Rochester, N.Y. In other embodiments, other suitable function generators and amplifiers can be used. The source 102 can be a single element transducer, a multiple element transducer, an extracorporeal ultrasound device, an intracavitary ultrasound device, and/or other devices or systems that can propagate nonlinear acoustic waves. For example, in one embodiment, the source 102 is a PZ 26 spherically focused piezoceramic crystal transducer made by Ferroperm Piezoceramics of Kvistgaard, Denmark that has a frequency of approximately 2 MHz, an aperture with a radius of approximately 22.5 mm, and a radius of curvature (i.e., focal length) of approximately 22.5 mm. In other embodiments, the source 102 can have different frequencies, aperture dimensions, and/or focal lengths to accommodate other therapeutic and diagnostic applications. The function generator 104 and the amplifier 106 can drive the source 102 to radiate high amplitude acoustic waves that propagate nonlinearly (e.g., forming shock waves) to a focus 120. The focus 120 is a point, plane, or region at which the intensity from the source 102 is the highest.

As shown in FIG. 1, the system 100 can further include a hydrophone 108 substantially aligned with the focus 120. The hydrophone 108 can be used to measure waveforms at the focus 120 (i.e., focal waveforms) after propagation through a medium. For example, in the illustrated embodiment, the hydrophone 108 is positioned in a tank of water 116 such that it can be used to measure pressure waveforms at the focus 120 (i.e. focal waveforms) after propagation through the water 116. The hydrophone 108 can also measure focal waveforms behind a tissue sample (e.g., ex vivo bovine liver, a tissue mimicking phantom, etc.) 118 (e.g., shown positioned in a tissue holder) after propagation through the water 116 and/or the tissue sample 118. In selected embodiments, the system 100 can include a positioning device 110 (e.g., a three-axis computer-controlled positioning system made by Velmex Inc. of Bloomfield, N.Y.) coupled to the source 102 to aid in aligning the focus 120 with the hydrophone 108.

In selected embodiments, the hydrophone 108 can be a fiber optic probe hydrophone ("FOPH") that has a large bandwidth and a small active diameter (e.g., approximately 100 μm) to capture high intensity nonlinear waveforms (e.g., sharp shock fronts) at a narrow focus. The hydrophone 108 can also be mechanically robust enough to withstand mechanical damage from cavitation (e.g., a FOPH 500 or a FOPH 2000 made by RP Acoustics of Leutenbach, Germany). The hydrophone 108 and/or additional hydrophones (not shown) can also be used to measure the axial and transverse beam profiles of the source 102.

As further shown in FIG. 1, the hydrophone 108 can be operably coupled to an oscilloscope 112 that can record the focal waveforms measured by the hydrophone 108 and other data measured by the system 100. In one embodiment, for example, the oscilloscope 110 is a LT344 digital oscilloscope made by Lecroy of Chestnut Ridge, NY that measures 500 megasamples per second. The oscilloscope 112, along with the function generator 104, the positioning device 110, and/or other portions of the system 100 can be coupled to a controller 114 (e.g., a computer) that can be used to control the function and movement of the system 100 and to analyze measured data. In other embodiments, the system 100 can include additional devices and/or some of the devices may be omitted from the system 100. For example, the system 100 can include a high-voltage probe (not shown) positioned in parallel with the source 102 to monitor the amplitude of the drive voltage to the source 102.

In operation, the system 100 can be used to predict parameters of nonlinear acoustic fields in tissue. The source 102 can first be positioned in the tank of water 116 without the tissue sample 118, and the focus 120 of the source 102 in water can be substantially aligned with the hydrophone 108 (e.g., using the positioning system 110). If the focal length (i.e., the distance from the source 102 to the focus 120) is unknown, the focal length can be experimentally obtained by propagating ultrasound waves through the tank of water 116 and detecting (e.g., with the hydrophone 108 and/or other suitable monitoring devices) the location where the ultrasound waves have the highest pressure.

Once the source 102 and the hydrophone 108 are properly aligned, the function generator 104 can drive the source 102 at a first voltage to propagate acoustic waves through the water 116. The hydrophone 108 can then measure the focal waveform in water, from which the focal pressure waveform can be determined and the focal peak positive pressure (i.e., the maximum compression), the focal peak negative pressure (i.e., the maximum rarefaction), the shock amplitude (i.e., the pressure jump of the steepest portion of the focal waveform), and the intensity can be calculated (e.g., via the controller 114). The function generator 104 can then drive the source 102 at a second voltage different from the first voltage, and the hydrophone 108 can measure the resultant focal waveform. These steps can be repeated for varying source voltages and the results can be compiled in a table as described in greater detail below.

In other embodiments, the focal pressure amplitude can be measured at low power outputs of the source 102 (e.g., under linear propagation conditions) by scanning the hydrophone 108 along the source axis and across an axis in the focal plane. In this embodiment, the hydrophone 108 can be an uncalibrated needle hydrophone (e.g., a GL-150-1A hydrophone with an active diameter of 150 μm made by Specialty Engineering Associates of Soquel, CA), a calibrated polyvinylidene fluoride ("PVDF") membrane hydrophone (e.g., an MHA-200 hydrophone with an active diameter of 200 μm and a sensitivity of 0.168 V/MPa made by NTR Systems of Seattle, Wash.), and/or other suitable monitoring devices known in the art.

In further embodiments, focal waveforms in water and in tissue can be modeled (i.e., rather than measured) for various source voltages and source pressures using a Khokhlov-Zabolotskaya-Kuznetsov ("KZK") nonlinear parabolic equation:

$$\frac{\partial}{\partial \theta}\left[\frac{\partial P}{\partial z} - NP\frac{\partial P}{\partial \theta} - A_w\frac{\partial^2 P}{\partial \theta^2} - A_t L(P)\right] = \frac{1}{4G}\Delta P, \quad \text{(Equation 1)}$$

where P is acoustic pressure normalized to the pressure amplitude at the source ($P=p/p_0$); $\theta$ is dimensionless retarded time ($\theta=2\pi f_0(t-x/c_0)$, where $c_0$ is the ambient sound speed); z is propagation distance normalized by the focal length ($z=x/F$, where F is the focal length); N is a parameter of nonlinearity ($N=2\pi F f_0 \beta p_0/c_0^3 \rho_0$, where $\rho_0$ is the density of the medium, $\beta$ is the nonlinear parameter of the medium, and $f_0$ is the source frequency); $A_w$ is a parameter of absorption in water ($A_w=\alpha_w F$ where $\alpha_w$ is the attenuation coefficient in water at the source frequency $f_0$); $A_t$ is a parameter of attenuation in tissue ($A_t=\alpha_t F$, where $\alpha_t$ is the attenuation coefficient in tissue at the source frequency $f_0$); L(P) is a linear operator that accounts for frequency dependent absorption and sound dispersion in tissue; and G is a parameter of diffraction (i.e., the linear focusing gain of the system, $G=\omega_0 r_0^2/2c_0$). As described in further detail below, the nonlinear parameter ($\beta$) of Equation 1 can be derived experimentally when it is unknown.

The boundary conditions of Equation 1 can be given at the source as a focused beam with initial harmonic waveform and uniform distribution (e.g., a piston source). If the boundary conditions are unknown, they can be experimentally defined (e.g., using the system 100 of FIG. 1) by measuring the focal pressure and beam dimensions with the hydrophone 108 and/or other suitable monitoring devices at low output levels (i.e., under linear acoustic propagation). The pressure amplitude then can be scaled linearly during modeling by increasing the driving voltage to the source, and Equation 1 can be used to determine pressure waveforms in and around the focus at higher source operation levels. For highly focused sources, such as those used during HIFU therapy, diffraction effects can be more accurately capture in the model using the Westervelt equation:

$$\frac{\partial p}{\partial t^2} - c_0^2 \Delta p = \frac{\beta}{\rho_0 c_0^2}\frac{\partial^2 p^2}{\partial t^2} + \frac{\alpha_w}{2c_0^3}\frac{\partial^3 p}{\partial t^3} + L_t(p) \quad \text{(Equation 2)}$$

where p is pressure; t is time; $c_0$ is the ambient sound speed; $\beta$ is the nonlinear parameter of the medium; $\rho_0$ is the density of the medium, $\alpha_w$ is the attenuation coefficient in water at the source frequency; and $L_t(p)$ is a linear operator that accounts for frequency dependent absorption and sound dispersion in tissue.

Figure 2A:
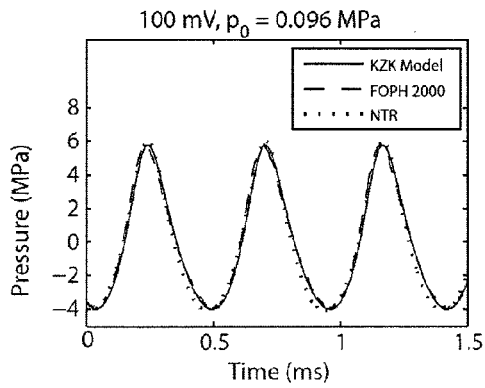
FIGS. 2A-2D are a series of graphs illustrating measured and modeled focal waveforms for increasing source outputs in accordance with embodiments of the present technology.
Figure 2B:
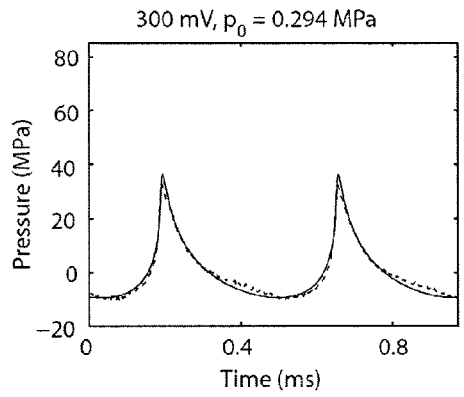
Figure 2C:
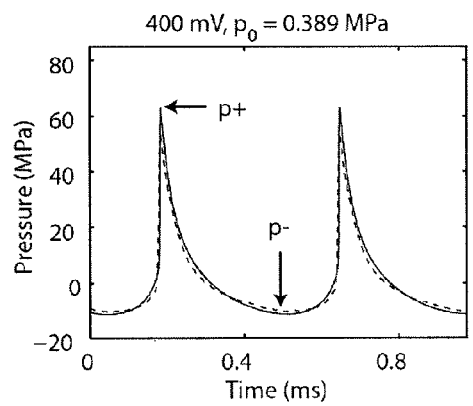
Figure 2D:
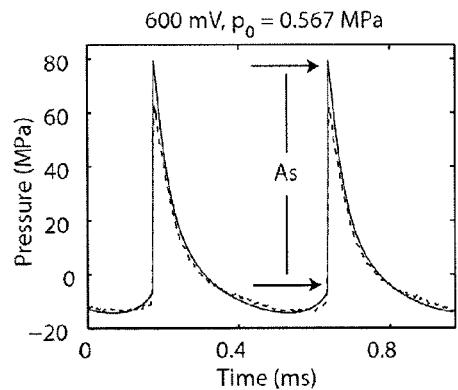

FIGS. 2A-2D are a series of graphs illustrating measured (e.g., using the system 100 of FIG. 1) and modeled (e.g., using Equation 1 or Equations 1 and 2) focal waveforms in water for increasing source outputs in accordance with embodiments of the present technology. FIG. 2A, for example, illustrates a measured focal waveform for an ultrasound source (e.g., a HIFU transducer with an operating frequency of 2.158 MHz and an aperture and focal length of approximately 45 mm) having a driving voltage of 100 mV and a modeled focal waveform with a corresponding initial pressure ($p_0$) of 0.096 MPa. FIGS. 2B-2D illustrate focal waveforms for increasing source voltages from 300 mV to 600 mV and for corresponding increasing initial pressures from 0.294 MPa to 0.567 MPa. The agreement between the measured and modeled focal waveforms demonstrates that focal waveforms can be accurately determined by direct measurements and modeling.

Referring to FIG. 2A, at low measured or modeled source outputs (e.g., approximately 100 mV) the focal waveform is harmonic and the peak positive pressure (p+) is equal to the negative pressure (p−). However, referring to FIGS. 2B-2D, at higher source outputs (e.g., 300 mV-600 mV) the focal waveforms are asymmetric such that the peak positive pressure (p+) is higher than the peak negative pressure (p−). As shown in FIGS. 2C and 2D, steep shock fronts with pressure jumps ($A_s$) develop in the focal waveforms at higher outputs (e.g., approximately 400 mV-600 mV).

Figure 3:
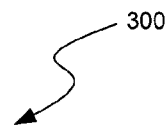
FIG. 3 is a table of acoustic field parameters for use with nonlinear derating methods in accordance with embodiments of the present technology.

FIG. 3 is a table 300 illustrating measured and/or modeled focal pressures for increasing source outputs in accordance with an embodiment of the present technology. For example, the columns under the title "HIFU TRANSDUCER FOCUSING IN WATER" show driving voltages to the source ($V_w$) and corresponding initial pressures ($p_0$) for which focal waveforms were measured (e.g., using the system 100 shown in FIG. 1) and/or modeled (e.g., using Equations 1 and/or 2) in water. The driving voltages and initial pressure amplitudes that correspond to the focal waveforms shown in FIGS. 2A-2D are indicated in bold italics. The columns in the table 300 under the title "PRESSURES AT THE FOCUS" include measured and/or modeled pressures of the focal waveforms (e.g., peak positive pressure, peak negative pressure, and shock amplitude).

The table 300 of measured and/or modeled focal waveforms in water can be used to determine the parameters of the focal waveforms in tissue. For example, a focal waveform (e.g., a desired peak positive pressure, shock amplitude, etc.) can be selected from the table 300 for use during ultrasound imaging or therapy, and the source voltage corresponding to the focal waveform in water can be scaled to account for losses over the path in tissue caused by the linear attenuation in tissue on the way to the focus. More specifically, if $\alpha$ is the attenuation coefficient in tissue at the source frequency and L is the depth of the focus in the tissue, the initial amplitude of the wave propagating in tissue should be $\exp(\alpha L)$ times higher than the initial amplitude of the wave in water to compensate for the pressure attenuation caused by the tissue on the way to the focus. Accordingly, the source voltage ($V_t$) required to generate the selected waveform in tissue can be calculated as follows:

$$V_t = V_w \exp(\alpha L), \quad \text{(Equation 3)}$$

where $V_w$ is a source voltage corresponding to the selected focal waveform in water, $\alpha$ is the attenuation coefficient in tissue at the source frequency, and L is the depth of the focus in tissue. For example, the source voltage in water ($V_w$) of a HIFU source having a source frequency of approximately 2.158 MHz and a depth of focus in tissue (L) of approximately 27 mm must be scaled by a scaling factor (i.e., exp ($\alpha$L)) of 1.64 to obtain the same focal waveform in tissue having an attenuation coefficient ($\alpha$) of 1.6 dB/cm at the source frequency. Therefore, Equation 3 can be used to determine a scaling factor for a source voltage in water for various focal waveforms to obtain the requisite source voltage to produce the focal waveform in tissue. As explained in greater detail below, the attenuation coefficient ($\alpha$) can be derived experimentally when it is unknown.

Referring again to FIG. 3, the derated source voltages can be compiled in the table 300 as shown in the columns under the title "HIFU TRANSDUCER FOCUSING IN TISSUE." A physician can reference the table 300 to obtain the source voltage required to transmit a focal waveform with a desired peak positive pressure, peak negative pressure, and/or shock amplitude in tissue. The pressure values in table 300 can also be used to determine other acoustic parameters (e.g., intensity, heating rates) of the ultrasound fields in the focus and, in some embodiments, these additional acoustic parameters are included in columns in the table 300 to provide further information related to the focal waveforms. In various embodiments, tables similar to the table 300 shown in FIG. 3 can be created for ultrasound sources having different beam profiles and/or source frequencies to determine the parameters of the acoustic field in tissue.

Figure 4:
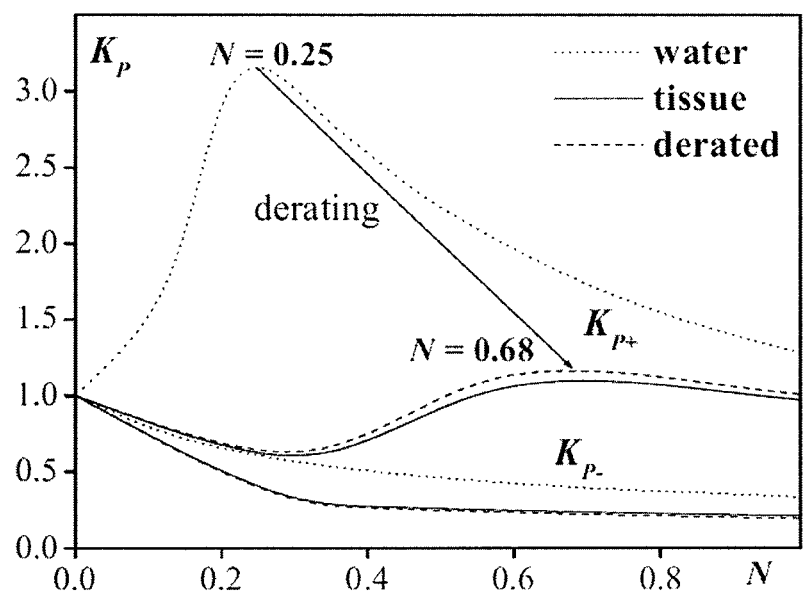
FIG. 4 is a graph illustrating the accuracy of a nonlinear derating method configured in accordance with an embodiment of the present technology.

FIG. 4 is a graph illustrating the accuracy of the nonlinear derating method described above. More specifically, FIG. 4 shows the modeled corrections (K) to the linear focusing gain (i.e., the quantity $K=p_F/Gp_0$, where $p_F$ is focal pressure, G is a linear focusing gain of 40, and $P_0$ is initial source pressure) for peak positive and negative pressures in focal waveforms in tissue and water as functions of the source pressure (i.e., parameter N$\square p_0$). The solid line and the dotted line correspond to the results of direct modeling (e.g., using Equation 1) of the wave propagation in tissue and in water, respectively. The arrow illustrates the effect of nonlinearly derating (e.g., using Equation 3) the modeled waveform in water to determine the results in tissue. The derated waveform (shown as dashed lines) and the directly modeled waveform in tissue have a difference of less than 8% for source outputs ranging from substantially linear focusing (e.g., N<0.1) to highly nonlinear focusing with high amplitude shocks in the focal waveform (e.g., N>0.25). Accordingly, numerical algorithms (e.g., Equation 1) together with the nonlinear derating method described above (e.g., Equation 3) can be used to accurately determine focal waveforms in tissue for both slightly distorted focal waveforms and in the presence of shocks.

Accordingly, the system 100 of FIG. 1 and Equations 1-3 in conjunction with the table 300 of FIG. 3 can be used to compare focal waveforms measured or modeled in water and scale the source output to generate the same focal waveform in tissue. By evaluating the acoustic field at the focus, the disclosed derating method takes into account the shape of the focal waveform and the nonlinear characteristics of the acoustic field, rather than conventional derating methods that only consider the acoustic field at the operational frequency of the source. Accordingly, the present derating method can be used to more accurately predict the parameters of nonlinear acoustic fields generated by high intensity focused ultrasound systems. The prediction of parameters of nonlinear acoustic fields can be used for protocol planning, estimating in situ heating rates, and to establish standards for safety and efficacy. For example, the nonlinear derating method described above can be used for a HIFU source to aid in planning a pulsing protocol that generates shock waves in tissue that cause millisecond boiling as described in U.S. patent application Ser. No. 12/085,368, filed Apr. 12, 2011, entitled "METHODS AND SYSTEMS FOR NON-INVASIVE TREATMENT OF TISSUE USING HIGH INTENSITY FOCUSED ULTRASOUND THERAPY," which is incorporated herein by reference in its entirety.

Figure 5:
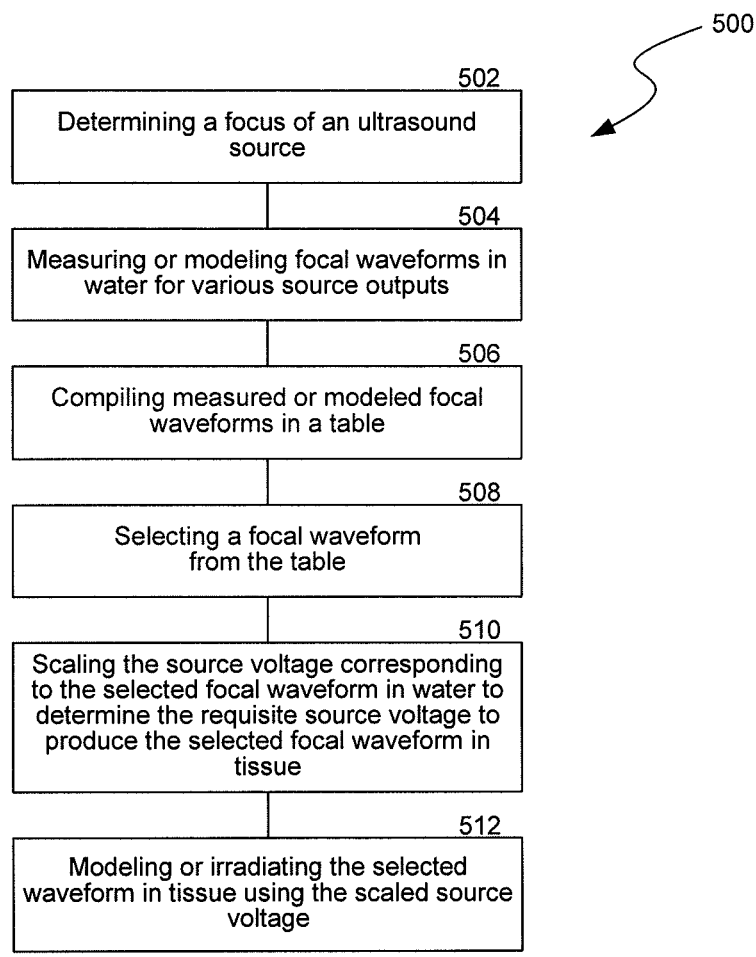
FIG. 5 is a block diagram illustrating a nonlinear derating method in accordance with an embodiment of the present technology.
Figure 6:
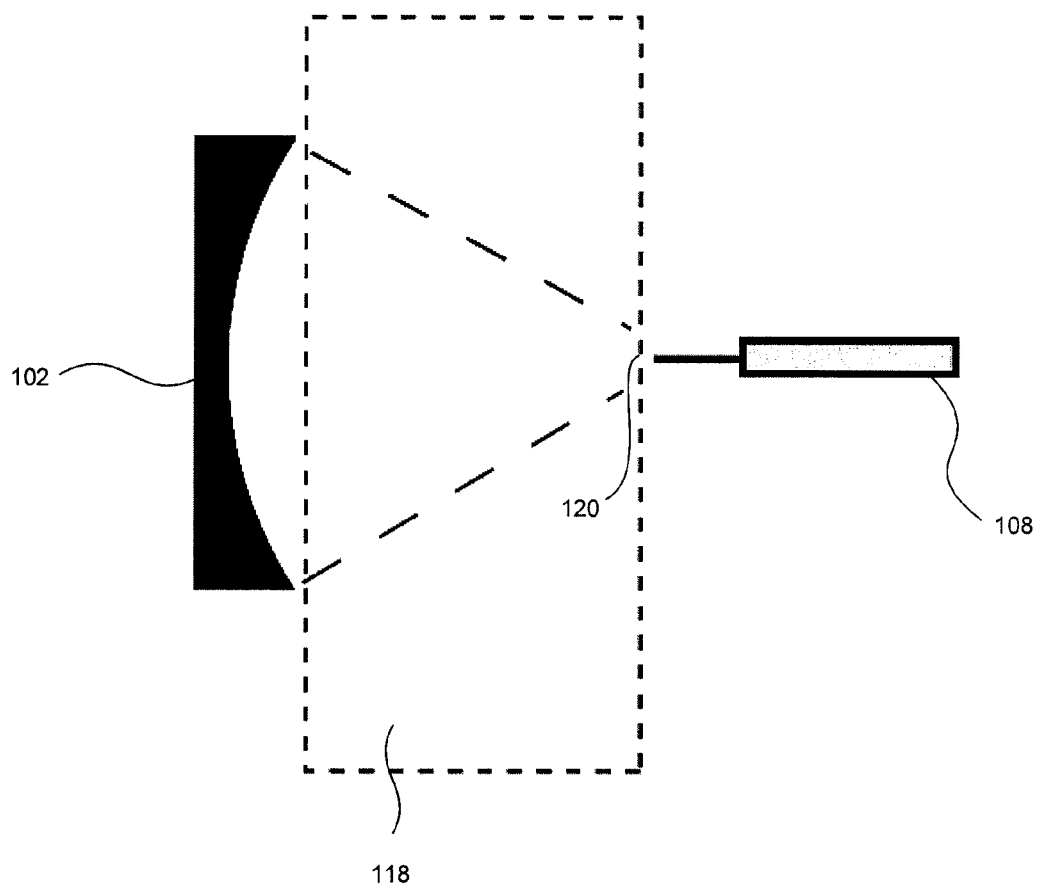
FIG. 6 is an enlarged schematic view of a portion of the ultrasound system of FIG. 1.

FIG. 5 is a block diagram illustrating a nonlinear derating method 500 in accordance with an embodiment of the present technology. The method 500 can include determining a focus of an ultrasound source (block 502), and measuring or modeling waveforms at the focus in water for various source outputs (block 504). As discussed above, the focus of the ultrasound source can be determined experimentally by irradiating acoustic waves in water to determine the region or point of peak pressure. A hydrophone (e.g., the hydrophone 108 described with reference to FIG. 1) and/or other monitoring devices can then be used to measure focal waveforms for various source outputs. In other embodiments, the focal waveforms in water can be modeled using a nonlinear KZK-type equation (e.g., Equation 1).

The measured or modeled waveforms can be compiled in a table (block 506), and a desired focal waveform can be selected from the table (block 508). The table can include features generally similar to the features in the table 300 shown in FIG. 3, such as various source voltages of a specific ultrasound source (e.g., a source having a certain beam profile or frequency) and corresponding parameters of the focal waveforms (e.g., peak positive pressure, shock amplitude, etc.) in water.

The source voltage in water corresponding to the selected focal waveform can then be scaled to account for the absorption of the wave caused by tissue (block 510). For example, Equation 3 scan be used to derate the source voltage in water and determine the appropriate source voltage to obtain the same focal waveform in tissue. An ultrasound source can then be calibrated to the scaled source voltage and irradiated into a patient to produce the selected waveform in tissue (block 512). In other embodiments, various source voltages can be scaled and compiled into a table for later reference. Therefore, the method 500 can be used to determine the increase in the source voltage necessary to overcome tissue attenuation to generate the same focal waveform in tissue as in water (e.g., the same focal pressures and same shape of nonlinearly distorted focal waveform). Accordingly, the method 500 can be used by physicians planning treatment protocols or ultrasound source manufacturers determining parameters for ultrasound devices.

In various embodiments, the attenuation coefficient of a tissue may be unknown and can be experimentally determined. For example, referring back to FIG. 1, the source 102 can be set at a relatively low output level such that acoustic propagation is linear (i.e., there is no harmonic content in the measured focal waveform) or slightly nonlinear (i.e., there are some harmonics in the measured focal waveform), and the hydrophone 108 can be used to measure focal waveforms in the water 116. The tissue sample 118 can then be positioned such that the back surface of the tissue sample 118 is proximate the focus 120 of the source 102 in subsequent ultrasound exposures. As shown in greater detail in FIG. 6, the hydrophone 108 can be positioned proximate the focus 120 behind the tissue sample 118 (e.g., within 1 mm of the focus 120), and the hydrophone 108 can measure focal waveforms from behind the tissue sample 118 for low or medium level source outputs. The source voltage can be increased until the measured focal waveform from behind the tissue sample 118 matches the measured focal waveform in water. The source outputs that generate the same focal waveform (i.e., the same focal pressure amplitude) in water and in tissue can then be used to solve for Equation 3 and determine the attenuation coefficient (α) of the tissue sample 118 and the scaling factor (i.e., exp(αL)).

In other embodiments, the measured focal waveform from behind the tissue sample 118 can be compared to the results of free-field modeling in water, e.g., using a KZK-type numerical model like Equation 1. The KZK-type numerical model can be calibrated by the free-field measurements and then used to perform simulations of the focal waveforms in water and tissue. For example, if the initial driving voltage to the source at low output in water corresponds to the initial pressure amplitude ($p_0$) in water (e.g., determined during modeling) that provides the same focal pressure amplitude in the tissue sample 118 (e.g., measured using the system 100), the initial pressure amplitude in the modeling can be scaled linearly with the increase of the driving voltage to the source 102. The modeled focal waveforms in water can then be matched with the focal waveform measured from behind the tissue sample 118 to determine the attenuation coefficient of the tissue sample 118 as described above.

Figure 7:
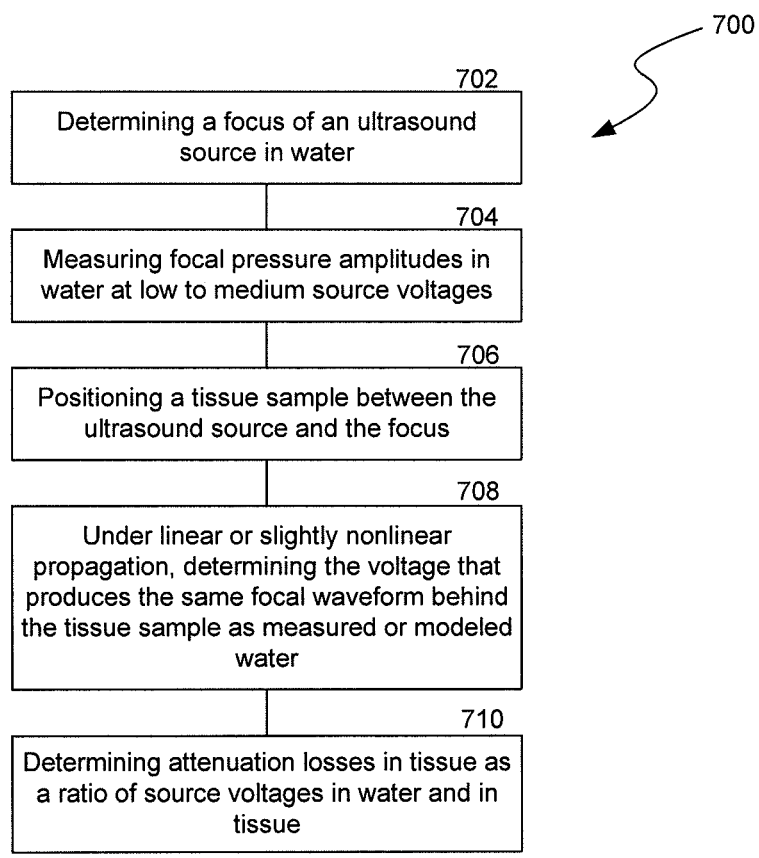
FIG. 7 is a block diagram illustrating a method of determining attenuation losses in tissue from in vitro measurements in accordance with an embodiment of the present technology.

FIG. 7 is a block diagram illustrating a method 700 for determining an attenuation coefficient in tissue in accordance with an embodiment of the present technology. The method 700 includes determining a focus of an ultrasound source in water (block 702), and measuring focal pressure amplitude in water at low to medium source voltages (i.e., linear propagation or slightly nonlinear propagation; block 704).

The method 700 can further include positioning a tissue sample between the ultrasound source and the focus (block 706) and, under linear or slightly nonlinear propagation, determining the source voltage that produces the same focal waveform behind the tissue sample as in water (block 708). For example, the source can operate at various low or medium source voltages until it generates a focal waveform in tissue that is the same as the focal waveform measured in water. In other embodiments, focal waveforms in water can be modeled using Equation 1 to determine the source voltage that provides the same focal waveform in water as measured in tissue. The attenuation losses in tissue can then be determined using the ratio of the source voltages that produce the same focal waveforms in tissue and in water (block 710).

In other embodiments, the attenuation coefficient can be determined by measuring the time to initiate boiling at the focus of an ultrasound source. Without being bound by theory, it is thought that in the instance of nonlinear fields that include shock waves at the focus, the absorption of ultrasound energy at the shock fronts becomes the dominant mechanism of tissue heating. Therefore, the heating rate (H) induced by an ultrasound wave containing shock fronts in the propagation medium (e.g., water, tissue) can be calculated using weak shock theory:

$$H = \frac{\beta f_0 A_s^3}{6\rho_0^4 c_0^2},$$ (Equation 4)

where $A_s$ is in situ shock amplitude (e.g., measured using the system 100 of FIG. 1), β is the coefficient of nonlinearity, $f_0$ is the source frequency, $c_0$ is the ambient sound speed, and $\rho_0$ is the density of the medium. When the heating rate (H) is sufficiently high to induce boiling in tissue within milliseconds (e.g., as in the case with some HIFU therapies), diffusion can be neglected and the time-to-boil ($t_b$) can be calculated according to:

$$t_b = \frac{\Delta T c_v}{H},$$ (Equation 5)

where ΔT is the change in temperature of the medium and $c_v$ is the specific heat of the tissue.

In further embodiments, the time to initiate boiling can alternatively be measured in situ and used to determine the attenuation coefficient of the tissue using Equations 4 and 5. For example, a millisecond-long pulse of a source output can be transmitted into the body, and the time-to-boil ($t_b$) can be measured. The in situ shock amplitude ($A_s^{(tissue)}$) can then be calculated as follows:

$$A_s^{(tissue)} = \sqrt[3]{\frac{6\Delta T c_v \rho_0^2 c_0^4}{f_0 \beta t_b}},$$ (Equation 6)

where ΔT is the change in temperature of the medium, $c_v$ is the specific heat of the tissue, $\rho_0$ is the density of the medium, $c_0$ is the ambient sound speed, $f_0$ is the source frequency, and β is the coefficient of nonlinearity.

Once the shock amplitude in tissue is calculated (e.g., using Equation 6), the driving voltage to the source that produces the same shock amplitude in water can be determined using a table of focal waveforms (e.g., the table 300 shown in FIG. 3). The ratio of source voltages that produce the same shock amplitudes in tissue and in water can then be used to solve for the attenuation coefficient (α) as follows:

$$\alpha = \frac{1}{L}\ln\left(\frac{V_t}{V_w}\right),$$ (Equation 7)

where L is the depth of the focus in the tissue, $V_t$ is the source voltage in tissue, and $V_w$ is the source voltage in water selected from a table (e.g., the table 300 of FIG. 3).

Figure 8:
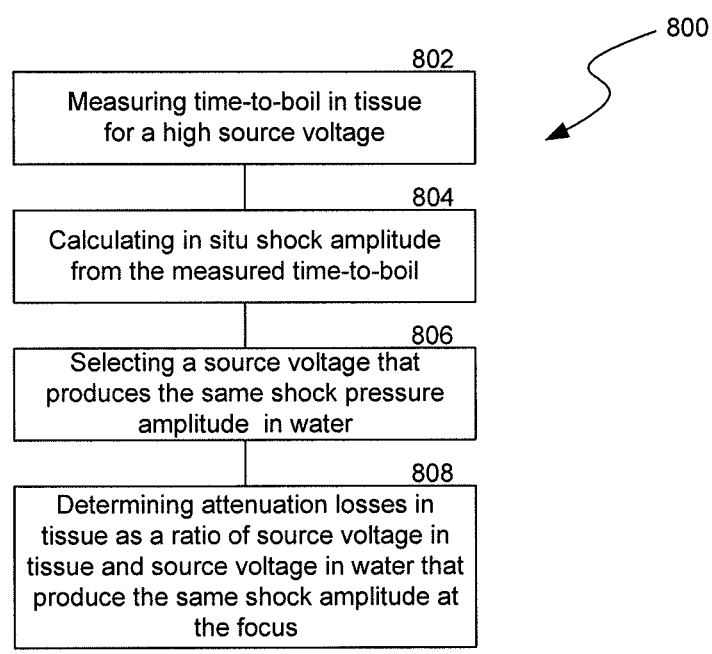
FIG. 8 is a block diagram illustrating a method of determining attenuation losses in tissue by measuring time-to-boil in tissue in accordance with an embodiment of the present technology.

FIG. 8 is a block diagram illustrating a method 800 of determining attenuation losses in tissue by measuring the time-to-boil in tissue in accordance with an embodiment of the present technology. The method 800 can include measuring the time-to-boil in tissue for a high transducer voltage (802), and calculating in situ shock amplitude from the measured time-to-boil using, e.g., Equation 6 (804). The time-to-boil can be measured in vitro (e.g., using the system 100 of FIG. 1) and/or in vivo (e.g., before a procedure).

The method 800 can continue by selecting a source voltage that produces the same shock amplitude in water (block 806). In various embodiments, a reference table of modeled focal waveforms and associated source voltages, such as the table 300 shown in FIG. 3, can be used to match the shock pressure amplitude to the corresponding initial pressure amplitude in water. The attenuation losses in tissue can then be determined as a ratio of the source voltage in tissue and the source voltage in water that produce the same shock amplitude at the focus using Equation 7 (block 808).

Figure 9:
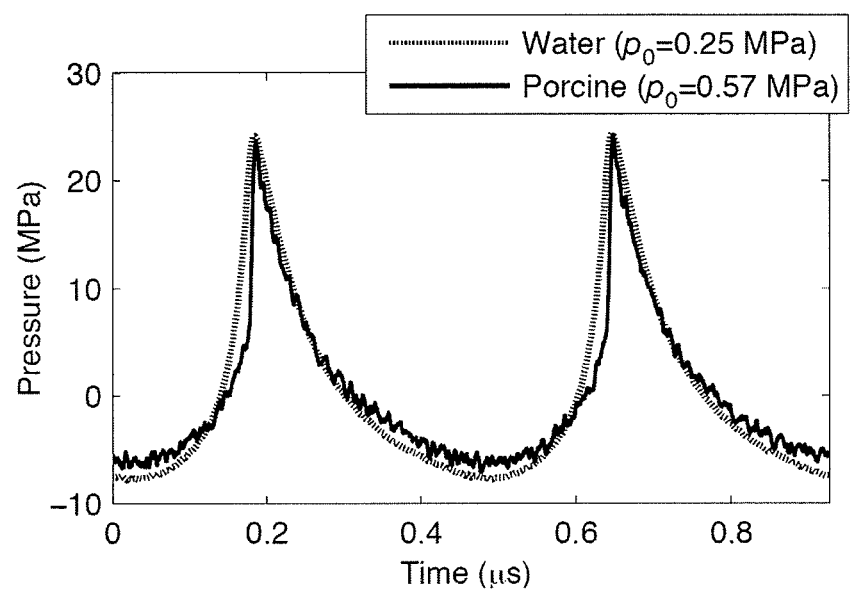
FIG. 9 is a graph illustrating shock fronts in focal waveforms measured in tissue and derated from measurements in water in accordance with an embodiment of the present technology.

In various embodiments, tissues may have a nonlinear parameter higher than that of water, and therefore the focal waveform in tissue may be steeper and contain more energy at higher harmonics than that predicted by the nonlinear derating method described above. FIG. 9, for example, illustrates focal waveforms measured after propagation in tissue (solid line) and derated from measurements in water (dotted line) using the nonlinear derating method described above (e.g., Equation 3). The measured focal waveform in tissue has the same peak pressures and overall shape as a derated focal waveform, but the measured focal waveform has a steeper shock front than that of the derated focal waveform, thereby indicating that the tissue has a higher nonlinear parameter than that of water.

In another aspect of the present technology, the difference in nonlinear parameters of tissue and water can be compensated for by increasing the initial pressure amplitude at the source. More specifically, the degree of nonlinear effects in a KZK model (e.g., determined using Equation 1) in a weakly absorptive medium (e.g., water or a water-like medium) can be determined by a parameter of nonlinearity ($N=2\pi F f_0 \beta p_0/c_0^3 \rho_0$), which is proportional to the product of the initial source pressure ($p_0$) and nonlinear parameter ($\beta$) of the propagation medium. A change in the nonlinear parameter ($\beta$) is therefore equivalent to an increase of the initial pressure amplitude. The dimensionless focal waveform ($p_F^{water,\beta}(t)/p_0$) in water with nonlinear parameter of $\beta$ will therefore be the same as the focal waveform ($p_F^{water,\beta^*}(t)/p_0^*$) in water-like medium with a nonlinearity $\beta^*$ if $\beta p_0 = \beta^* p_0^*$.

Accordingly, measured or modeled focal waveforms in water (e.g., the focal waveforms compiled in the table 300 shown in FIG. 3) can be scaled to focal waveforms in a water-like medium with a different nonlinear parameter $\beta^*$ than water. For example, a focal waveform in a water-like medium with nonlinear parameter of $\beta^*$ at a voltage that is $\beta/\beta^*$ lower than the voltage in water with a nonlinear parameter of $\beta$ will have the same shape as the focal waveform in water, but will be $\beta/\beta^*$ lower than in water. Therefore, if:

$$V_{\beta^*}^{(water)} = \frac{\beta}{\beta^*} V_{\beta}^{(water)}, \quad \text{(Equation 8)}$$

then the focal waveforms are related according to:

$$p(t)_{F,\beta^*}^{(water)} = \frac{\beta}{\beta^*} V_{F,\beta}^{(water)}, \quad \text{(Equation 9)}$$

where $p(t)_{F,\beta}^{(water)}$ is the focal waveform in water with nonlinear parameter of $\beta$ produced with the source voltage $V_\beta^{(water)}$ and $p(t)_{F,\beta}^{(water)}$ is the focal waveform in a water-like medium with nonlinear parameter of $\beta^*$ produced with the source voltage $V_{B^*}^{(water)}$. Equations 8 and 9 can be used to determine the source voltage and/or initial source pressure and corresponding focal waveform in a water-like medium having different nonlinear parameter $\beta^*$ than water. Once the data in the table is scaled to correct for the different nonlinear parameter ($\beta^*$), the measured focal waveform in tissue can be compared to the focal waveform from the scaled table to determine attenuation in tissue using Equation 7.

When the nonlinear parameter in tissue ($\beta^*$) is unknown, it can be determined experimentally. For example, referring back to FIG. 1, the tissue sample 118 can first be positioned between the source 102 and the hydrophone 108, and the function generator 104 can drive the source 102 at moderate outputs such that several harmonics are present in the focal waveform. The hydrophone 108 can then measure the degree of the waveform distortion. Using measured and/or modeled (e.g., generated using the KZK-type equation) focal waveforms in water (e.g., from the table 300 of FIG. 3), the initial source pressures and focal waveforms in water can be scaled using Equations 8 and 9 to obtain a new set of tables that correspond to focal waveforms for water-like medium with various different nonlinear parameters. Using the scaled tables, the nonlinear parameter which results in the modeled focal waveforms that best match the measured focal waveforms (e.g., peak pressures) and the measured waveform distortion can be determined. Once the nonlinear parameter is determined, the tissue attenuation can be derived using Equation 7 as described above.

Figure 10A:
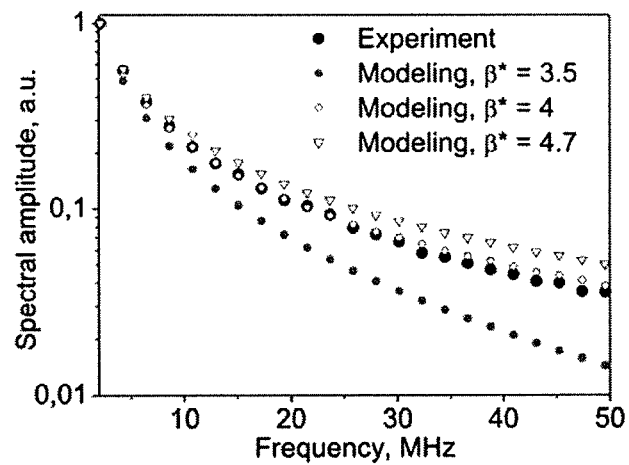
FIG. 10A is a graph illustrating spectral amplitude curves for experimentally determining a nonlinear parameter in accordance with an embodiment of the present technology.

In other embodiments, the degree of nonlinear distortion can be quantified by comparing the harmonic content of measured and modeled focal waveforms. FIG. 10A, for example, is a graph illustrating spectrum amplitude curves of a measured focal waveform (e.g., measured using the system 100 of FIG. 1) and various modeled focal waveforms (e.g., simulated using Equation 1) in accordance with an embodiment of the present technology. The modeled spectrum amplitude curves are simulated using various nonlinear parameters (e.g., 3.5, 4, 4.7, etc.) and plotted against the measured spectrum amplitude curve. The nonlinear parameter of the tissue can then be determined by selecting the nonlinear parameter that results in a modeled curve with a spectrum decay that is most similar to that of the measured spectrum decay. In the illustrated embodiment, for example, the measured spectrum decay is most similar to the modeled curve having a nonlinear parameter ($\beta$) of 4, and therefore the nonlinear parameter of the tissue is 4.

Figure 10B:
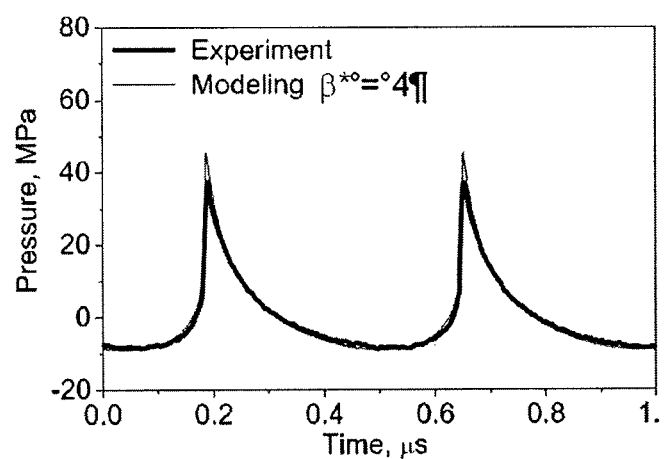
FIG. 10B is a graph illustrating a measured focal waveform and a modeled focal waveform having a nonlinear parameter determined using FIG. 10A in accordance with an embodiment of the present technology.

The nonlinear parameter can then be used in Equation 1 to model the focal waveform of nonlinear waves in tissue and in water. FIG. 10B, for example, is a graph illustrating a measured focal waveform ("Experiment") and a modeled focal waveform ("Modeling") with the selected nonlinear parameter. The selected nonlinear parameter generates a focal waveform that is substantially similar to the measured focal waveform. Therefore, Equation 1 can be used to accurately model focal waveforms for media having a different nonlinear parameter than water.

Figure 11A:
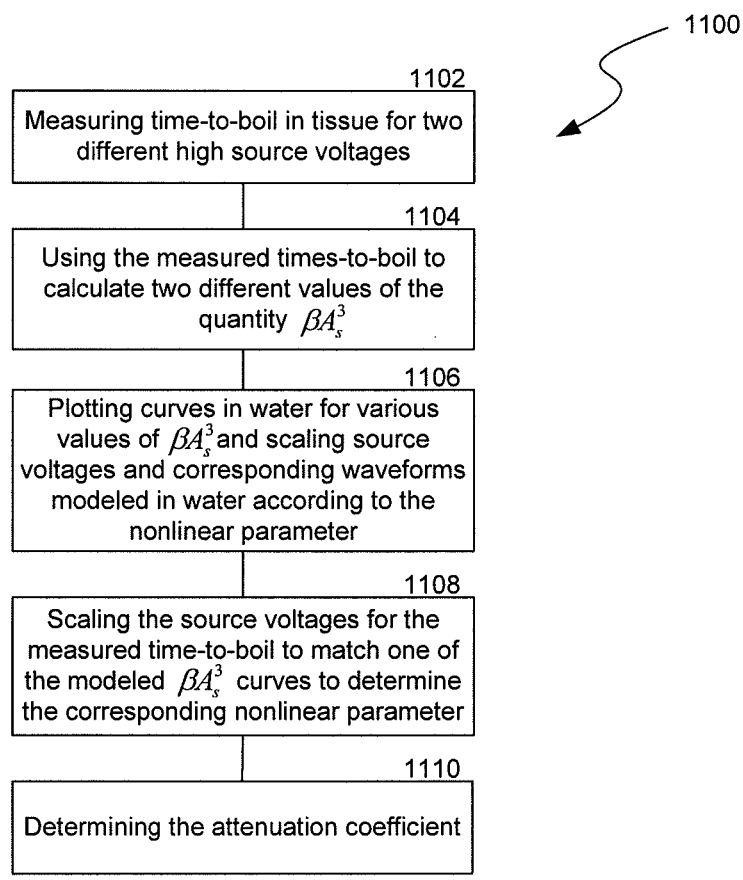
FIG. 11A is a block diagram illustrating a method of determining attenuation losses and nonlinear parameters in tissue by measuring time-to-boil in tissue in accordance with another embodiment of the present technology.

FIG. 11A is a block diagram illustrating a method 1100 of determining attenuation losses and nonlinear parameters by measuring the time-to-boil in tissue in accordance with another embodiment of the present technology. The method 1100 can include measuring the time-to-boil in tissue (e.g., in vitro or in vivo) at two different source voltages (block 1102), and using the measured time-to-boil to calculate:

$$\beta^* A_s^3 (V_{sourse\_1}^{(tissue)}) = \Omega/t_{b\_1} \text{ and} \quad \text{(Equation 10)}$$

$$\beta^* A_s^3 (V_{sourse\_2}^{(tissue)}) = \Omega/t_{b\_2}, \quad \text{(Equation 11)}$$

where $\beta A_s^3$ is inversely proportional to time-to-boil and $$\Omega = \frac{6\Delta T c_v \rho_0^2 c_0^4}{f_0}$$

is a known coefficient (block 1104).

Figure 11B:
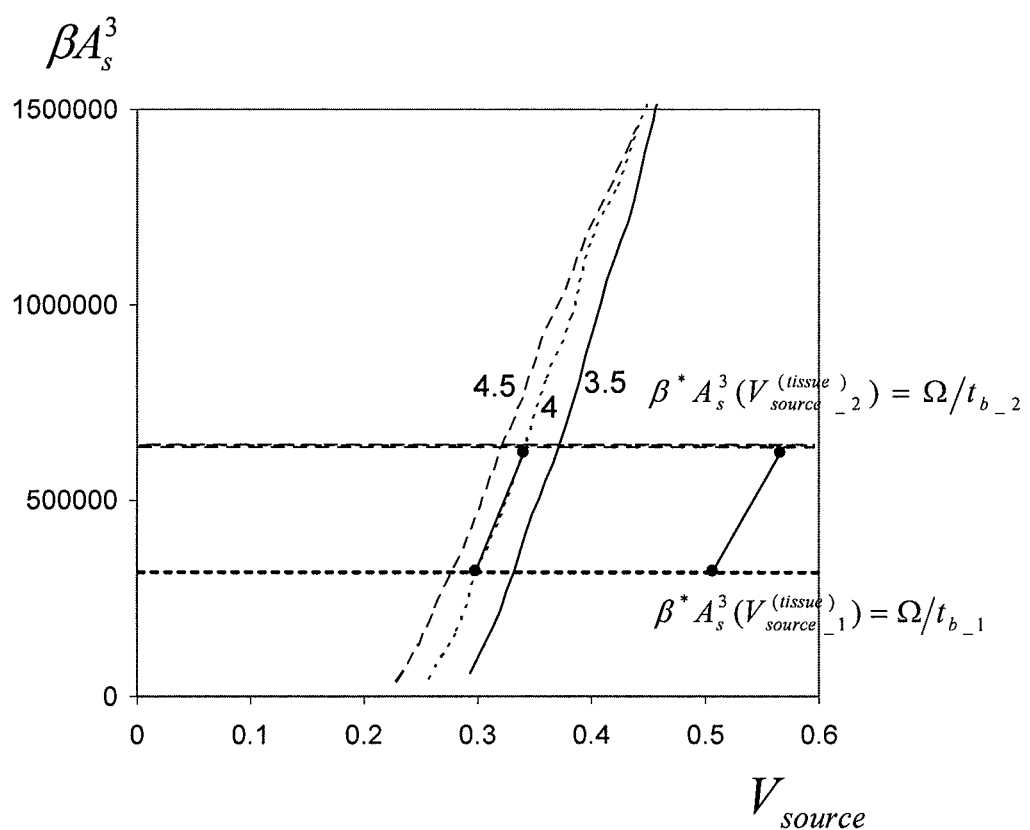
FIG. 11B is a graph illustrating $\beta A_s^3$ curves used with the method of FIG. 11A to determine a nonlinear parameter of a tissue in accordance with an embodiment of the present technology.

The method 1100 can further include plotting curves of $\beta A_s^3$ in water for various values of $\beta A_s^3$ (block 1106). FIG. 11B, for example, is a graph illustrating a variety of such curves for $\beta=3.5, 4, 4.5$. If the shock amplitude ($A_s$) corresponds to the source voltage in water with a nonlinear parameter $\beta$, then the shock amplitude in a water-like medium with a nonlinear parameter $\beta^*$ will be $$\frac{\beta}{\beta^*} A_s,$$

and the source voltage will be $$\frac{\beta}{\beta^*} V_{source}.$$

Using this scaling factor, the source voltages and corresponding focal waveforms in a table of measured and/or modeled focal waveforms in water can be scaled for the nonlinear parameter.

The nonlinear parameter can then be selected by scaling the source voltages for the measured time-to-boil and matching the resultant curves with the modeled curves to determine the corresponding nonlinear parameter (block 1108). In FIG. 11B, for example, the measured curve fits best with the curve that has a nonlinear parameter of 4. The attenuation coefficient can then be determined according to Equation 7 as described above. Using the derived attenuation coefficient and nonlinear parameter, the focal waveforms in tissue can be predicting using modeled focal waveforms in water-like medium having the same nonlinear parameter as the tissue.

From the foregoing, it will be appreciated that specific embodiments of the technology have been described herein for purposes of illustration, but that various modifications may be made without deviating from the disclosure. For example, the ultrasound system 100 of FIG. 1 can include additional devices and/or systems that generate and/or measure high amplitude nonlinear waveforms. As another example, the system 100 can be used to determine the focal waveforms, attenuation coefficients, and nonlinear parameters in media using various ultrasound sources with different beam profiles. Certain aspects of the new technology described in the context of particular embodiments may be combined or eliminated in other embodiments. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:
1. A derating method, comprising:
generating a nonlinear focal waveform in water from an ultrasound source at a first source voltage ($V_w$); and
setting a second source voltage ($V_t$) of the ultrasound source according to

$$V_t = V_w \exp(\alpha L),$$

where $\alpha$ is an attenuation coefficient of a tissue at the frequency of the ultrasound source and L is a depth of the focus in the tissue, and wherein the ultrasound source is configured to generate the focal waveform in the tissue when the ultrasound source is set at the second voltage ($V_t$).

2. The method of claim 1 wherein generating the nonlinear focal waveform in water comprises irradiating a nonlinear acoustic wave from the ultrasound source set at the first source voltage ($V_w$).

3. The method of claim 1 wherein generating the nonlinear focal waveform in water comprises modeling the nonlinear focal waveform according to $$\frac{\partial}{\partial \theta}\left[\frac{\partial P}{\partial z} - NP\frac{\partial P}{\partial \theta} - A_w \frac{\partial^2 P}{\partial \theta^2} - A_t L(P)\right] = \frac{1}{4G}\Delta P,$$

where P is acoustic pressure normalized to pressure amplitude at the ultrasound source, $\theta$ is dimensionless retarded time, z is propagation distance normalized by a focal length, N is a dimensionless parameter of nonlinearity, $A_w$ is a dimensionless parameter of absorption in water, $A_t$ is a dimensionless parameter of attenuation in tissue, L(P) is a dimensionless operator of frequency dependent absorption and sound dispersion in tissue, and G is dimensionless parameter of diffraction.

4. The method of claim 3, further comprising:
measuring dimensions of a focal region of the ultrasound source;
measuring waveforms in the focal region of a linear acoustic wave from the ultrasound source, wherein the waveforms have a measured focal pressure; and
modeling focal waveforms in water to match the dimensions of the focal region and the measured focal pressure to determine boundary conditions for $$\frac{\partial}{\partial \theta}\left[\frac{\partial P}{\partial z} - NP\frac{\partial P}{\partial \theta} - A_w \frac{\partial^2 P}{\partial \theta^2} - A_t L(P)\right] = \frac{1}{4G}\Delta P.$$

5. The method of claim 1, further comprising:
at least one of measuring and modeling a focal waveform in water at a water source voltage ($V_w$), wherein the water source voltage ($V_w$) generate at least one of linear acoustic waves and slightly nonlinear acoustic waves;
measuring the same focal waveform in the tissue, wherein the ultrasound source is set at a tissue source voltage ($V_t$); and
determining the attenuation coefficient ($\alpha$) according to $$\alpha = \frac{1}{L}\ln\left(\frac{V_t}{V_w}\right).$$

6. The method of claim 1, further comprising:
measuring a first time interval to induce boiling of the tissue with the ultrasound source voltage set at a high source voltage;
calculating shock amplitude ($A_s^{(tissue)}$) from the time-to-boil according to $$A_s^{(tissue)} = \sqrt[3]{\frac{6\Delta T c_v \rho_0^2 c_0^4}{f_0 \beta t_b}},$$

where $\Delta T$ is a change in temperature of the medium, $c_v$ is specific heat of the tissue, $\rho_0$ is density of the tissue, $c_0$ is ambient sound speed, $f_0$ is source frequency, and $\beta$ is a coefficient of nonlinearity; and
calculating the attenuation coefficient ($\alpha$) of the tissue according to $$\alpha = \frac{1}{L}\ln\left(\frac{V_t}{V_w}\right),$$

wherein $V_t$ is a source amplitude in tissue that produces the shock amplitude and $V_w$ is a source amplitude in water that produces the same shock amplitude in water.

7. The method of claim 1 wherein:
generating the nonlinear acoustic wave comprises generating a plurality of nonlinear acoustic waves in water, wherein the ultrasound source is set to a plurality of different source voltages, $(V_{wN})$ to generate the corresponding plurality of nonlinear acoustic waves;
determining the focal waveform of the nonlinear acoustic wave comprises determining a plurality of focal waveforms corresponding to the plurality of nonlinear acoustic waves; and
the method further comprises—
selecting one of the plurality of focal waveforms; and
calculating a source voltage $(V_{tN})$ according to $$V_{tN} = V_{wN} \exp(\alpha L),$$

where $(V_{wN})$ is the voltage of the ultrasound source used to generate the selected focal waveform in water, $\alpha$ is the attenuation coefficient of the tissue, and L is the focal length, and wherein the ultrasound source is configured to generate the selected focal waveform in the tissue when the ultrasound source is set at the source voltage $(V_{tN})$.

8. The method of claim 1 wherein the tissue has a different nonlinear parameter than a nonlinear parameter of water, and wherein the method further comprises:
scaling a source pressure amplitude to account for the nonlinear parameter of the tissue; and
scaling a focal pressure amplitude measured or modeled in water to account for the nonlinear parameter of the tissue.

9. The method of claim 1, further comprising:
irradiating acoustic waves in at least one of water and tissue; and
measuring a region of highest pressure of the acoustic waves, wherein the region corresponds to a focus of the ultrasound source, and wherein the distance from the ultrasound source to the focus is the focal length.

10. The method of claim 1, further comprising:
measuring a first time-to-boil in tissue for a first high source voltage, wherein the first high source voltage produces a first shock wave in the tissue;
measuring a second time-to-boil for a second high source voltage, wherein the second high source voltage produces a second shock wave in the tissue;
determining a nonlinear parameter from the first and second time-to-boil.

11. A derating method, comprising:
selecting a focal waveform and a corresponding first voltage $(V_w)$ of an ultrasound source that generates the focal waveform in water, wherein the focal waveform is nonlinear;
selecting an attenuation of a tissue;
setting a second voltage $(V_t)$ that generates the focal waveform in the tissue according to $$V_t = V_w \exp(\alpha L),$$

where $\alpha$ is an attenuation coefficient of the tissue at the frequency of the ultrasound source, and L is a focal length of the ultrasound source; and
at least one of computer modeling and irradiating a nonlinear ultrasound wave with the ultrasound source set at the second voltage, wherein the nonlinear ultrasound wave forms the focal waveform in the tissue.

12. The method of claim 11, further comprising:
determining a nonlinear parameter of the tissue in vitro or in vivo; and
scaling a source pressure amplitude and a focal pressure amplitude of a focal beat waveform in water according to the nonlinear parameter.

13. The method of claim 12, wherein determining the nonlinear parameter comprises:
measuring a time-to-boil in the tissue or in a tissue sample for a source voltage;
calculating a quantity $\beta A_s^3$, where $\beta$ is a nonlinear parameter and $A_s$ is in situ shock amplitude that is inversely proportional to the time-to-boil and a constant $\Omega$;
modeling a plurality of $\beta A_s^3$ curves in water, wherein $\beta$ is varied in each of the curves; and
scaling source voltages for the measured time-to-boil to match one of the curves, wherein the value of $\beta$ of the curve that matches the measured time-to-boil curve is the nonlinear parameter of the tissue.

14. The method of claim 11, further comprising deriving at least one of the attenuation coefficient of the tissue and a nonlinear parameter of the tissue by measuring a time-to-boil in the tissue.

15. An ultrasound system, comprising:
an ultrasound source configured to propagate nonlinear acoustic waves; and
a controller having instructions for
generating a nonlinear acoustic wave from the ultrasound source in water, wherein the ultrasound source is set to a first source voltage $(V_w)$;
determining a focal waveform of the nonlinear acoustic wave; and
determining a second source voltage $(V_t)$ the ultrasound source according to $$V_t = V_w \exp(\alpha L),$$

where $\alpha$ is an attenuation coefficient of a tissue at the frequency of the ultrasound source and L is a focal length of the ultrasound source; and
wherein the ultrasound source is configured to generate the focal waveform in the tissue when the ultrasound source is set at the second voltage $(V_t)$.

16. The ultrasound system of claim 15 wherein the controller further includes instructions for comparing focal waveforms in water modeled by a Khokhlov-Zabolotskaya-Kuznetsov ("KZK") type numerical model with the focal waveforms measured in the tissue.

17. The ultrasound system of claim 15 wherein the controller further includes instructions for:
measuring dimensions of a focal region of the ultrasound source;
measuring waveforms in the focal region of a linear acoustic wave from the ultrasound source, wherein the waveforms have a measured focal pressure; and
modeling focal waveforms in water to match the dimensions of the focal region and the measured focal pressure to determine boundary conditions for the KZK-type numerical model.

18. The ultrasound system of claim 15 wherein the controller further includes instructions for determining the attenuation coefficient of the tissue.

19. The ultrasound system of claim 15 wherein the ultrasound source is configured to irradiate high intensity focused ultrasound (HIFU) waves that form shock fronts at a focus of the ultrasound source.

20. The ultrasound system of claim 15 wherein the controller further includes instructions for deriving a nonlinear parameter of the tissue.

\* \* \* \* \*

UNITED STATES PATENT AND TRADEMARK OFFICE
CERTIFICATE OF CORRECTION

PATENT NO. : 8,668,658 B2
APPLICATION NO. : 13/236531
DATED : March 11, 2014
INVENTOR(S) : Vera A. Khokhlova et al.

It is certified that error appears in the above-identified patent and that said Letters Patent is hereby corrected as shown below:

In the Specification

In column 5, line 40, Delete "$G = \omega_0 r_0^2 / 2c_0$)." and insert -- $G = \omega_0 r_0^2 / 2c_0 F$ ). --, therefor.

In column 5, line 61-62, Delete "$\frac{\partial p}{\partial t^2} - c_0^2 \Delta p$" and insert -- $\frac{\partial^2 p}{\partial t^2} - c_0^2 \Delta p$ --, therefor.

In column 11, line 46, Delete "$V_{B^*}^{(water)}$" and insert -- $V_{\beta^*}^{(water)}$ --, therefor.

In column 12, line 43, Delete "$\beta^* A_s^3 (V_{sourse\_1}^{(tissue)}) = \Omega / t_{b\_1}$" and insert -- $\beta^* A_s^3 (V_{source\_1}^{(tissue)}) = \Omega / t_{b\_1}$ --, therefor.

In column 12, line 46, delete "$\beta^* A_s^3 (V_{sourse\_2}^{(tissue)}) = \Omega / t_{b\_2}$," and insert -- $\beta^* A_s^3 (V_{source\_2}^{(tissue)}) = \Omega / t_{b\_2}$ --, therefor.

Signed and Sealed this
Twentieth Day of January, 2015

Michelle K. Lee
*Deputy Director of the United States Patent and Trademark Office*

CERTIFICATE OF CORRECTION (continued)
U.S. Pat. No. 8,668,658 B2

In the Claims

In column 16, line 5, in claim 12, after "focal" delete "beat".

In column 16, line 35, in claim 15, before "the" insert -- of --.

In column 16, line 46, in claim 16, delete "fbr" and insert -- for --, therefor.